US008071647B2

(12) United States Patent
Shudo et al.

(10) Patent No.: US 8,071,647 B2
(45) Date of Patent: Dec. 6, 2011

(54) METHOD FOR TREATMENT OF ADHESION OF THE INTESTINES

(75) Inventors: Koichi Shudo, Tokyo (JP); Hiroyuki Kagechika, Tokyo (JP); Hiroshi Fukasawa, Tokyo (JP); Tetsuro Matsuishi, Tokyo (JP); Naoko Katsumura, Tokyo (JP); Miwako Ishido, Tokyo (JP)

(73) Assignee: Kemphys Ltd.

( * ) Notice: Subject to any disclaimer, the term of this patent is extended or adjusted under 35 U.S.C. 154(b) by 0 days.

(21) Appl. No.: 12/872,171

(22) Filed: Aug. 31, 2010

(65) Prior Publication Data

US 2010/0324134 A1 Dec. 23, 2010

Related U.S. Application Data

(63) Continuation of application No. 12/559,268, filed on Sep. 14, 2009, which is a continuation of application No. 12/065,099, filed as application No. PCT/JP2006/317720 on Sep. 7, 2006, now abandoned.

(30) Foreign Application Priority Data

Sep. 9, 2005 (JP) ................................. 2005-261775

(51) Int. Cl.
*A61K 31/196* (2006.01)

(52) U.S. Cl. ...................................................... 514/563

(58) Field of Classification Search ........................ None
See application file for complete search history.

(56) References Cited

U.S. PATENT DOCUMENTS

| 4,703,110 | A | 10/1987 | Shudo |
| 5,776,915 | A | 7/1998 | Peterson et al. |
| 5,929,069 | A | 7/1999 | Shudo |
| 6,589,989 | B1 | 7/2003 | Bollag et al. |
| 2005/0234130 | A1 | 10/2005 | Nagai et al. |
| 2008/0021108 | A1 | 1/2008 | Shudo et al. |
| 2008/0139842 | A1 | 6/2008 | Shudo et al. |
| 2008/0182905 | A1 | 7/2008 | Takenaga et al. |
| 2008/0207768 | A1 | 8/2008 | Shudo et al. |
| 2008/0255069 | A1 | 10/2008 | Shudo et al. |
| 2009/0253796 | A1 | 10/2009 | Nagai et al. |
| 2010/0004203 | A1 | 1/2010 | Shudo et al. |

FOREIGN PATENT DOCUMENTS

| EP | 1500401 | 1/2005 |
| JP | 61-22047 | 1/1986 |
| JP | 61-76440 | 4/1986 |
| JP | 7-101857 | 4/1995 |
| JP | 10-59951 | 3/1998 |
| WO | 99/09969 | 3/1999 |
| WO | 03/89005 | 10/2003 |
| WO | 2005/087129 | 9/2005 |
| WO | 2007/007198 | 1/2007 |

OTHER PUBLICATIONS

Ellis, H., European Journal of Surgery (Suppl.), (1997), (577), pp. 5-9 (Abstract).*
Extended European Search Report issued in connection with the counterpart European application, on Jun. 17, 2010.
Morzsik et al., "Retiniods as Scavengers and Gastric Cytoprotection in Animals, Human Beings and Patients with Peptic Ulcer", Oxygen Free Radicals and Scavengers in the Natural Sciences, Jan. 1, 1993, pp. 329-338.
Sako et al, "4-[3, 5-Bis(trimethylsilyl)benzamido] benzoic acid (TAC-101) induces apoptosis in colon cancer partially through the induction of Fas expression", In Vivo, vol. 19, No. 1, Jan. 2005, pp. 125-132.
Desreumaux et al. "Attenuation of colon inflammation through activators of the retinoid X receptor (RXR)/peroxisome proliferator-activated receptor gamma γ (PPARγ) heterodimer: A basis for new therapeutic strategies", Journal of Experimental Medicine, vol. 193, No. 7, Apr. 2, 2001, pp. 827-838.
Kagechika et al. "Retinobenzoic Acids. 1. Structure-Activity Relationships of Aromatic Amides with Retinoidal Activity" *J Med. Chem.* vol. 31, No. 11, pp. 2182-2192, 1988.
Evans, R.M. "The Steroid and Thyroid Hormone Receptor Superfamily" *Science* vol. 240, pp. 889-895, 1988.
Petkovich et al. "A Human Retinoic Acid Receptor Which Belongs to the Family of Nuclear Receptors" *Nature* vol. 330, pp. 444-450, 1987.
Mangelsdorf et al. "Nuclear Receptor that Identifies a Novel Retinoic Acid Response Pathway" *Nature* vol. 345, pp. 224-229, 1990.
Hashimoto, Y. "Retinobenzoic Acids and Nuclear Retinoic Acid Receptors" *Cell Structure and Function* vol. 16, No. 2, pp. 113-123, 1991.
Hashimoto et al. "Expression of Retinoic Acid Receptor Genes and the Ligand-Binding Selectivity of Retinoic Acid Receptors (RAR's)" *Biochem. Biophys. Res. Commun.* vol. 166, No. 3, pp. 1300-1307, 1990.
Wright et al. "Vitamin A Therapy in Patients with Crohn's Disease" *Gastroenterology* vol. 88, No. 2, pp. 512-514, 1985.
Selenkow, H.A. "Remission of Hyperthyroidism and Oral Contraceptive Therapy" *The Journal of the American Medical Association* (*JAMA*) vol. 252, No. 17, p. 2463, 1984.
Gold et al. "The Retinoids and Inflammatory Bowel Disease" *Arch. Dermatol.* vol. 124, No. 3, pp. 325-326, 1988. Godfrey et al. "Treatment of Severe Acne with Isotretinoin in Patients with Inflammatory Bowel Disease" *Br. J. Dermatol.* vol. 123, No. 5, pp. 653-655, 1990.
Harewood et al. "Treatment of Acute Myeloid Leukemia M3 in a Patient with Chrone's Disease" *Cancer Invest.* vol. 18, No. 1, p. 98, 2000.
De Thé et al. "Retinoids: 10 Years on." Ed. J.H. Saurat, Basel Karger, pp. 2-9, 1991.

(Continued)

*Primary Examiner* — Phyllis G. Spivack
(74) *Attorney, Agent, or Firm* — Greenblum & Bernstein, P.L.C.

(57) ABSTRACT

Method for suppressing adhesion of the intestines or therapeutic treatment of adhesion of the intestines comprising administering to a patient in need thereof a therapeutically effective amount of 4-[(5,6,7,8-tetrahydro-5,5,8,8-tetramethyl-2-naphthalenyl)carbamoyl]benzoic acid. There is also provided a medicament for suppressing adhesion of the intestines and/or therapeutic treatment of bowel diseases such as inflammatory bowel diseases, including Crohn's disease, which comprises as an active ingredient a retinoid such as, for example, 4-[(5,6,7,8-tetrahydro-5,5,8,8-tetramethyl-2-naphthalenyl)carbamoyl]benzoic acid.

20 Claims, No Drawings

OTHER PUBLICATIONS

Yamakawa et al. "Retinobenzoic Acids. 5. Reinoidal Activities of Compounds Having a Trimethylsilyl or Trimethylgermyl Group(s) in Human Promyelocytic Leukemia Cells HL-60" *J. Med. Chem.* vol. 33, No. 5, pp. 1430-1437, 1990.

Wallace et al. "An Orally Active Inhibitor of Leukotriene Synthesis Accelerates Healing in a Rat Model of Colitis" *Am. J Physiol.* vol. 258, pp. G527-G534, 1990.

Rohrmann et al. "Association Between Serum Concentrations of Micronutrients and Lower Urinary Tract Symptoms in Older Men in the Third National Health and Nutrition Examination Survey" *Urology* vol. 64, No. 3, pp. 504-509, 2004.

Basu et al. "Vitamin A Homeostasis and Diabetes Mellitus" *Nutrition* vol. 13, No. 9, pp. 804-806, 1997.

Tuitoek et al. "Streptozotocin-Induced Diabetes in Rats is Associated with Impaired Metabolic Availability of Vitamin A (Retinol)" *British Journal of Nutrition* vol. 75, pp. 615-622, 1996.

Driscoll et al. "Vitamin A Status Affects the Development of Diabetes and Insulitis in BB Rats" *Metabolism* vol. 45, No. 2, pp. 248-253, 1996.

Yanagi et al. "Anti-120-kDa α-Fodrin Immune Response with Th1-Cytokine Profile in the NOD Mouse Model of Sjögren's Syndrome" *Eur. J. Immunol.* vol. 28, pp. 3336-3345, 1998.

Hunter et al. "Retinoic Acid Stimulates Neurite Outgrowth in the Amphibian Spinal Cord" *Proc. Natl. Acad. Sci. USA* vol. 88, pp. 3666-3670, 1991.

Wuarin et al. "Retinoids Increase Perinatal Spinal Cord Neuronal Survival and Astroglial Differentiation" *Int. J. Devl. Neuroscience* vol. 8, No. 3, pp. 317-326 (1990).

Haskell et al. "Effect of Retinoic Acid on Nerve Growth Factor Receptors" *Cell Tissue Res.* vol. 247, pp. 67-73, 1987.

Quinn et al., "Enhanced Neuronal Regeneration by Retinoic Acid of Murine Dorsal Root Ganglia and of Fetal Murine and Human Spinal Cord in Vitro" *In Vitro Cell. Dev. Biol.* vol. 27A, pp. 55-62, 1991.

Mey, J. "New Therapeutic Target for CNS Injury? The Role of Retinoic Acid Signaling after Nerve Lesions" *J. Neurobiol.* vol. 66, pp. 757-779, 2006.

Taha et al. "Effect of Retinoic Acid on Tibial Nerve Regeneration After Anastomosis in Rats: Histological and Functional Analyses" *Transpl. Proc.* vol. 36, pp. 404-408, 2004.

Mozsik et al. "Mechanisms of Action of Retinoids in Gastrointestinal Mucosal Protection in Animals, Human Healthy Subjects and Patients" *Life Sci.* vol. 69, No. 25-26, pp. 3103-3112, 2001.

Kagechika, H. "Vitamin A no Kino to sono Seigyo Bunshi" *Vitamins* vol. 77, No. 9, pp. 501-511, 2003.

Minagawa et al. "4-[3,5-bis(trimethylsilyl)benzamido] Benzoic Acid Inhibits Angiogenesis in Colon Cancer Through Reduced Expression of Vascular Endothelial Growth Factor" *Oncol. Res.* vol. 14, No. 9, pp. 407-414, 2004.

Shisui et al. "Hikanshiki Retinoid (ACR) wa Rat Daichozengan Byohen oyobi Shuyo Hassei o Yokusei shi Hito Daichogan Saibokabu ni oite apoptosis o Yudo suru," 64th Annual Meeting of the Japanese Cancer Association, Sep. 14-16, 2005, vol. 64, pp. 210, Article No. PP1-0479, Aug. 15, 2005.

The Merck Manual, 17th edition (1999), pp. 308-311.

\* cited by examiner

METHOD FOR TREATMENT OF ADHESION OF THE INTESTINES

CROSS-REFERENCE TO RELATED APPLICATIONS

This application is a continuation of application Ser. No. 12/559,268, filed Sep. 14, 2009, which is a continuation of application Ser. No. 12/065,099 which is a national stage of PCT/JP2006/317720, filed Sep. 7, 2006, which claims priority to Japanese Application No. 2005-0261775, filed Sep. 9, 2005. The disclosures of application Ser. Nos. 12/559,268 and 12/065,099, and PCT/JP2006/317720 are incorporated by reference herein in their entireties.

TECHNICAL FIELD

The present invention relates to a medicament for preventive and/or therapeutic treatment of a bowel disease such as inflammatory bowel diseases.

BACKGROUND ART

Bowel diseases are diseases with abnormal condition of small intestine or large intestine, which are accompanied with major symptoms including diarrhea (bacterial and viral infectious diarrhea, diarrhea caused by inflammatory bowel diseases, irritable bowel syndrome, or drug-induced enteritis and the like), constipation, or mucous bloody stool or the like. Among them, inflammatory bowel disease including ulcerative colitis (UC) and Crohn's disease (CD) is a chronic nonspecific inflammatory disease of the bowel which is frequently observed in Western countries, and the number of patients with the disease has been rapidly increasing also in Japan. Although a cause of the inflammatory bowel disease has not yet been identified, it is considered that the onset of the disease involves complicated participations of genetic, immunologic, and environmental medicinal factors.

For treatment of Crohn's disease, in order to control abnormally activated immunological reactions, nutrition therapy is generally applied to reduce exposure to food antigen which causes a stress to gastrointestinal tract. However, because the nutrition therapy alone is not expected to be effective for ulcerative colitis, an adrenal corticosteroid such as prednisolone is administered. As drug therapies, 5-aminosalicylic acid (tradename: Pentasa) and salazosulfapyridine (tradename; Salazopyrin), which are known to suppress inflammation-inducing substances (inflammatory cytokines, leukotriene, active oxygens and the like), have been generally used, and for patients with severer symptoms than moderate, adrenal corticosteroids (tradename; Prednisolone, Rinderon, and the like), cyclosporine (tradename: Sandimmune) and FK506 (tradename: Prograf) as immunosuppressant agents have been used. However, no medicament has been developed which exhibits remarkable effectiveness against inflammatory bowel disease or has reduced adverse effects.

Retinoic acid (vitamin A acid), an active metabolite of vitamin A, has extremely important physiological functions, e.g., inducing differentiation of immature cells under development processes toward mature cells having specific functions, acceleration of cell proliferation, and life support action. It has been revealed that various vitamin A derivatives synthesized so far also have similar physiological functions, for example, the benzoic acid derivatives disclosed in Japanese Patent Unexamined Publication (KOKAI) Nos. (Sho) 61-22047/1986 and (Sho) 61-76440/1986, and the compounds described in Journal of Medicinal Chemistry, 1988, Vol. 31, No. 11, p. 2182. "Retinoids" is a general term for retinoic acid and the aforementioned compounds having retinoic acid-like biological activities.

For example, it was proved that all-trans retinoic acid binds as a ligand to the retinoic acid receptor (RAR) present in cellular nucleus, which belongs to the intranuclear receptor super family (Evans, R. M., Science, 240, p. 889, 1988), and regulates proliferation and differentiation of animal cells or cellular mortalities (Petkovich, M., et al., Nature, 330, pp. 444-450, 1987). In addition, as for the expression of physiological activities of retinoic acid, the existence of retinoid X receptor (RXR of which ligand is 9-cis-retinoic acid) has been elucidated. The retinoid X receptor has been revealed to control the expression of the physiological activities of the retinoic acid by inducing or suppressing the transcription of a target gene by forming a dimer between the retinoic acid receptor (RAR) (Mangelsdorf, D. J. et al., Nature, 345, pp. 224-229).

It has also been suggested that the aforementioned compounds having the retinoic acid-like biological activities, e.g., 4-[(5,6,7,8-tetrahydro-5,5,8,8-tetramethyl-2-naphthalenyl) carbamoyl]benzoic acid: Am80, also bind to RAR in similar manners to retinoic acid to exhibit their physiological actions (see, Hashimoto, Y., Cell Struct. Funct., 16, pp. 113-123, 1991; Hashimoto, Y., et al., Biochem. Biophys. Res. Commun., 166, pp. 1300-1307, 1990). Clinically, these compounds were found to be useful for therapeutic and preventive treatments of vitamin A deficiency disease, hyperkeratosis of epithelial tissue, rheumatism, delayed allergy, bone diseases, leukemia and certain types of cancer.

As for a relation between retinoids and bowel diseases such as inflammatory bowel disease, a supply of Vitamin A to patients with Crohn's disease was studied. However, the study was reported to be ineffective (Gastroenterology, 88, pp. 512-514, 1985). Drug therapies by using retinoids have been applied for psoriasis and acute promyelocytic leukemia (APL), and several clinical cases were reported in which all-trans retinoic acid or analogues thereof was administered to the patients who were also suffering from Crohn's disease. However, effectiveness of retinoids against Crohn's disease was not clarified (The Journal of the American Medical Association (JAMA), 252, pp. 2463, 1984; Arch. Dermatol., 124, pp. 325-326, 1988; Br. J. Dermatol., 123, pp. 653-655, 1990; Cancer Invest., 18, p. 98, 2000).

DISCLOSURE OF THE INVENTION

Object to be Achieved by the Invention

An object of the present invention is to provide a medicament that is capable of exhibiting high effectiveness against bowel diseases. In particular, the object of the present invention is to provide a medicament that can achieve excellent preventive and/or therapeutic effect against inflammatory bowel diseases including ulcerative colitis and Crohn's disease.

Means to Achieve the Object

The inventors of the present invention conducted various researches to achieve the foregoing object. As a result, they found that retinoids such as retinoic acid had excellent preventive and/or therapeutic effects against the bowel diseases including inflammatory bowel diseases, and thus achieved the present invention.

According to the present invention, provided is a medicament for preventive and/or therapeutic treatment of a bowel disease, which comprises a retinoid as an active ingredient.

According to preferred embodiments of the above invention, provided are the aforementioned medicament, wherein the bowel disease is an inflammatory bowel disease, irritable bowel syndrome, duodenal ulcer, acute enteritis, protein losing gastroenteropathy, colon cancer, ileus, apendicitis, hemorrhagic colitis, intestinal tuberculosis, intestinal Behcet's disease, or diverticulitis of colon; and the aforementioned medicament, wherein the bowel disease is Crohn's disease.

According to further preferred embodiments of the above invention, provided are the aforementioned medicament, wherein the retinoid is non-natural retinoid; and the aforementioned medicament, wherein the retinoid has a basic skeleton comprising an aromatic ring bound with an aromatic carboxylic acid or tropolone by means of a bridging group.

According to still further preferred embodiments of the above invention, provided are the aforementioned medicament, wherein the retinoid is a retinoid binds to retinoic acid receptor (RAR) subtype α and subtype β; the aforementioned medicament, wherein the retinoid is a retinoid binds to retinoid X receptor X (RXR); the aforementioned medicament, wherein the retinoid has a basic skeleton comprising a substituted phenyl group bound with benzoic acid or tropolone by means of a bridging group; the aforementioned medicament, wherein the retinoid is 4-[(5,6,7,8-tetrahydro-5,5,8,8-tetramethyl-2-naphthalenyl)carbamoyl]benzoic acid or 4-[(3,5-bis-trimethylsilylphenyl)carboxamido]benzoic acid; the aforementioned medicament, wherein the retinoid comprises dibenzo[b,f][1,4]thiazepinylbenzoic acid as a basic skeleton; the aforementioned medicament, wherein the retinoid is 4-[2,3-(2,5-dimethyl-2,5-hexano)dibenzo[b,f][1,4]-thiazepin-11-yl]benzoic acid; and the aforementioned medicament, wherein the retinoid is 4-[5-(4,7-dimethylbenzofuran-2-yl)pyrrol-2-yl]benzoic acid.

From another aspect, provided are use of the above retinoid for manufacture of the aforementioned medicament; and a method for preventive and/or therapeutic treatment of a bowel disease comprising the step of administering an effective amount of the above retinoid to a mammal including a human.

BEST MODE FOR CARRYING OUT THE INVENTION

In the specification, the term "retinoid" means compounds that bind to receptors required for all trans-retinoic acid and 9-cis-retinoic acid to exhibit physiological functions thereof, and thereby exhibit actions similar to those of retinoic acid or a part of the actions, and the term means compounds that have at least one retinoid-like action, for example, one or more of cell differentiating action, cell proliferation promoting action, life supporting action, and the like. Whether a certain compound is a retinoid or not can be readily determined by the method described in H. de The, A. Dejean, "Retinoids; 10 years on.", Basel, Karger, 1991, pp. 2-9. Further, while retinoids generally have a property of binding to a retinoic acid receptor (RAR), and sometimes have property of binding to RXR together with RAR, the retinoid used as the active ingredient of the medicament of the present invention preferably binds to the subtype α (RARα) and the subtype β (RARβ) of RAR, and more preferably binds to the subtype α (RARα) and the subtype β (RARβ) and does not substantially bind to the subtype γ (RARγ) of RAR. Further, among these retinoids, those bind to RXR are also preferred. A binding to the retinoic acid receptor subtypes can also be readily determined by the method described in the aforementioned publication.

As the active ingredient of the medicament of the present invention, any of natural retinoids or non-natural retinoids may be used. Preferably, non-natural retinoid may be used. As the non-natural retinoids, those having a basic skeleton comprising an aromatic ring bound with an aromatic carboxylic acid or tropolone by means of a bridging group may be used.

More specifically, as non-natural retinoids, those represented by the following general formula: B-X-A (wherein B represents an aromatic group which may be substituted, X represents a bridging group, and A represents a carboxylic acid-substituted aromatic group or tropolonyl group) can be used.

As the aromatic group represented by B, a phenyl group which may have a substituent is preferred. Type, number, and substituting position of the substituent on the phenyl group are not particularly limited. As the substituent on the phenyl group, for example, a lower alkyl group can be used (in the specification, the term "lower" means a carbon number of 1 to about 6, preferably 1 to 4). As the lower alkyl group, an alkyl group having a linear or branched chain is preferred, and more specific examples include methyl group, ethyl group, n-propyl group, isopropyl group, n-butyl group, sec-butyl group, tert-butyl group, and the like. Other examples of the substituent on the phenyl group include, for example, a lower alkoxyl group such as methoxy group, a halogen atom (the halogen atom may be any of fluorine atom, chlorine atom, bromine atom, and iodine atom), a lower alkyl-substituted silyl group such as trimethylsilyl group, and the like. As the phenyl group, for example, a phenyl group substituted with 2 to 4 of lower alkyl groups, a phenyl group substituted with 1 or 2 of tri(lower alkyl)silyl group, and the like are preferred, and a phenyl group substituted with 2 to 4 of alkyl groups, a phenyl group substituted with 2 of trimethylsilyl groups, and the like are more preferred.

When two of the lower alkyl groups substituting on the phenyl group are adjacent to each other, they may combine together to form one or two, preferably one of 5- or 6-membered ring together with the ring-constituting carbon atoms of the phenyl group to which they bind. The ring formed as described above may be saturated or unsaturated, and one or more lower alkyl groups such as methyl group and ethyl group may substitute on the ring. On the aforementioned formed ring, preferably 2 to 4 of methyl groups, more preferably 4 of methyl groups, may substitute. For example, it is preferred that two adjacent lower alkyl groups which substitute on the phenyl ring combine together to form 5,6,7,8-tetrahydronaphthalene ring, 5,5,8,8-tetramethyl-5,6,7,8-tetrahydronaphthalene ring, or the like. As the aromatic group represented by B, an aromatic heterocyclic group may also be used. Examples of such retinoid include a retinoid wherein B is a benzofuranyl group which may have a substituent, preferably benzofuran-2-yl group, particularly preferably 4,7-dimethylbenzofuran-2-yl group.

As the carboxylic acid-substituted aromatic group represented by A, a carboxylic acid-substituted phenyl group, a carboxylic acid-substituted heterocyclic group, and the like can be used, and 4-carboxyphenyl group is preferred. Examples of the heterocyclic carboxylic acid constituting the carboxylic acid-substituted heterocyclic group represented by A include, for example, pyrimidine-5-carboxylic acid, and the like. As the tropolonyl group represented by A, tropolon-5-yl group is preferred. On the ring of the carboxylic acid-substituted aromatic group or tropolonyl group, one or more substituents may exist.

Type of the bridging group represented by X is not particularly limited, and examples include, for example, —NHCO—, —CONH—, —N($R^A$)— ($R^A$ represents a lower alkyl group, for example, cyclopropylmethyl group and the like), —C($R^B$)($R^C$)— ($R^B$ and $R^C$ independently represent hydrogen atom, a lower alkyl group, and the like). Further, X may be a divalent aromatic group. For example, X may be pyrrol-diyl group, or the like. Furthermore, the bridging group represented by X and the aromatic group represented by B may combine together to form a ring structure. For example, the basic skeleton of the retinoid represented by B-X-A may be dibenzo[b,f][1,4]thiazepinylbenzoic acid or dibenzo[b,f][1,4]diazepinylbenzoic acid. In the specification, the term "basic skeleton" means a main chemical structure for one or more arbitrary substituents to bind thereto.

As preferred retinoids, for example, retinoids comprising a phenyl-substituted carbamoylbenzoic acid or a phenyl-substituted carboxamidobenzoic acid as a basic skeleton can be used. Various retinoids comprising a phenyl-substituted carbamoylbenzoic acid or a phenyl-substituted carboxamidobenzoic acid as a basic skeleton are known. Typical examples of retinoids having a phenyl-substituted carbamoylbenzoic acid as a basic skeleton include Am80 (4-[(5,6,7,8-tetrahydro-5,5,8,8-tetramethyl-2-naphthalenyl)carbamoyl]benzoic acid (refer to Hashimoto, Y., Cell Struct. Funct., 16, pp. 113-123, 1991; Hashimoto, Y., et al., Biochem. Biophys. Res. Commun., 166, pp. 1300-1307, 1990), and typical examples of retinoids having a phenyl-substituted carboxamidobenzoic acid include Tac101 (4-[(3,5-bis-trimethylsilylphenyl)carboxamido]benzoic acid (J. Med. Chem., 33, pp. 1430-1437, 1990).

Preferred retinoids include, for example, compounds represented by the following general formula (I):

[Formula 1]

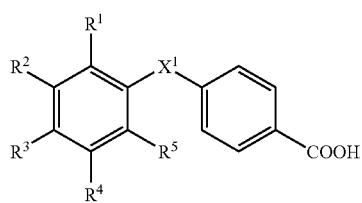

wherein $R^1$, $R^2$, $R^3$, $R^4$, and $R^5$ independently represent hydrogen atom, a lower alkyl group, or a lower alkyl-substituted silyl group, when two of adjacent groups among $R^1$, $R^2$, $R^3$, $R^4$, and $R^5$ are lower alkyl groups, they may combine together to form a 5- or 6-membered ring together with the carbon atoms of the benzene ring to which they bind (this ring may have one or more alkyl groups), and $X^1$ represents —CONH— or —NHCO—.

In the aforementioned general formula (I), as the lower alkyl group represented by $R^1$, $R^2$, $R^3$, $R^4$, and $R^5$, a linear or branched alkyl group having 1 to about 6 carbon atoms, preferably 1 to 4 carbon atoms, can be used. For example, methyl group, ethyl group, n-propyl group, isopropyl group, n-butyl group, sec-butyl group, tert-butyl group, and the like can be used. On the aforementioned lower alkyl group, one or more arbitrary substituents may exist. Examples of the substituents include, for example, hydroxyl group, a lower alkoxyl group, a halogen atom, and the like. Examples of the lower alkyl-substituted silyl group represented by $R^1$, $R^2$, $R^3$, $R^4$, and $R^5$ include, for example, trimethylsilyl group, and the like.

Two of adjacent lower alkyl groups selected from the group consisting of $R^1$, $R^2$, $R^3$, $R^4$, and $R^5$ may combine together to form one or two, preferably one of 5- or 6-membered ring together with the carbon atoms of the benzene ring to which they bind. The ring formed as described above may be saturated or unsaturated, or an aromatic ring, and one or more lower alkyl groups such as methyl group and ethyl group may substitute on the ring. As the alkyl group which may substitute on the ring, a linear or branched alkyl group having 1 to about 6 carbon atoms, preferably 1 to 4 carbon atoms, can be used. For example, methyl group, ethyl group, and the like can be used, and preferably 2 to 4 of methyl groups, more preferably 4 of methyl groups, may substitute. For example, it is preferred that 5,6,7,8-tetrahydronaphthalene ring, 5,5,8,8-tetramethyl-5,6,7,8-tetrahydronaphthalene ring, or the like is formed by the benzene ring on which $R^2$ and $R^3$ substitute, and $R^2$ and $R^3$.

Examples of other preferred retinoids include, for example, retinoids comprising dibenzo[b,f][1,4]thiazepinylbenzoic acid or dibenzo[b,f][1,4]-diazepinylbenzoic acid as the basic skeleton represented by B-X-A. Examples of such retinoids are described in, for example, Japanese Patent Unexamined Publication (KOKAI) No. 10-59951. Particularly preferred examples of such retinoids include, for example, HX630 (4-[2,3-(2,5-dimethyl-2,5-hexano)dibenzo[b,f][1,4]-thiazepin-11-yl]benzoic acid) and LE135 (4-(5H-7,8,9,10-tetrahydro-5,7,7,10,10-pentamethylbenzo[e]naphtho[2,3-b][1,4]diazepin-13-yl)benzoic acid). Further, examples of retinoids wherein X is —N($R^A$)—, and B is an aromatic heterocyclic carboxylic acid include, for example, 2-[2-(N-5,6,7,8-tetrahydro-5,5,8,8-tetramethyl-2-naphthalenyl-N-cyclopropylmethyl)amino]pyrimidine-5-carboxylic acid. The aforementioned HX630 and 2-[2-(N-5,6,7,8-tetrahydro-5,5,8,8-tetramethyl-2-naphthalenyl-N-cyclopropylmethyl)amino]pyrimidine-5-carboxylic acid are retinoids known as ligands for the receptor RXR. Further, examples of retinoids wherein X is a divalent aromatic group include, for example, 4-[5-(4,7-dimethylbenzofuran-2-yl)pyrrol-2-yl]benzoic acid. Examples of the compound wherein A is a tropolonyl group include, for example, 5-[[5,6,7,8-tetrahydro-5,5,8,8-tetramethyl-2-naphthalenyl]carboxamido]tropolone, and the like.

As the active ingredient of the medicament of the present invention, salts of the above retinoids may be used. For example, physiologically acceptable salts including metal salts such as sodium salts, potassium salts, magnesium salts, and calcium salts, ammonium salts, organic amine salts such as triethylamine salts, and ethanolamine salts, and the like can be used as the active ingredient of the medicament of the present invention. As the active ingredient of the medicament of the present invention, a prodrug of the above retinoid may be used. The term "prodrug" means a compound or a salt thereof which is, after oral or parenteral administration to a mammal, subjected to a structural change such as hydrolysis in vivo, preferably in blood, to produce the above retinoid or a salt thereof. For example, various means for producing prodrugs from pharmaceutical compounds having carboxylic acid, amino group, hydroxyl group or the like are known, and one of ordinary skill in the art can choose appropriate means. Types of the prodrug of the retinoid or a salt thereof are not particularly limited. For example, where a retinoid has carboxylic acid, an example includes a prodrug wherein the carboxylic acid is converted into an alkoxycarbonyl group.

Preferred examples include ester compounds such as those formed with methoxycarbonyl group or ethoxycarbonyl group. It should be understood that the term "retinoid" used in the specification encompasses the aforementioned prodrugs.

The aforementioned retinoid may have one or more asymmetric carbons depending on the types of substituents, and any optical isomers based on these asymmetric carbons, any mixtures of optical isomers, racemates, diastereoisomers based on two or more asymmetric carbons, any mixtures of diastereoisomers, and the like can be used as the active ingredient of the medicament of the present invention. Furthermore, geometrical isomers based on cis- or trans-configuration of double bond, any mixtures of geometrical isomers, and any hydrates or solvates of the compounds in free forms or in the form of a salt can also be used as the active ingredient of the medicament of the present invention.

The medicament of the present invention can be used for preventive and/or therapeutic treatment of a bowel disease. Examples of the bowel disease include, for example, inflammatory bowel disease (ulcerative colitis and Crohn's disease), irritable bowel syndrome, duodenal ulcer, acute enteritis, protein losing gastroenteropathy, colon cancer, ileus (enterostasis), apendicitis, hemorrhagic colitis, intestinal tuberculosis, intestinal Behcet's disease, and diverticulitis of colon. Examples of preferred diseases applicable by the medicament of the present invention include bowel diseases with inflammation in the intestine. Among the bowel diseases accompanying inflammation, inflammatory bowel disease is a preferred applicable target of the medicament of the present invention, and Crohn's disease is a particularly preferred applicable target of the medicament of the present invention. Effectiveness of the medicament of the present invention against bowel diseases such as inflammatory bowel disease can be readily confirmed by one of ordinary skill in the art according to the methods specifically described in the examples of the specification.

The medicament of the present invention comprises, as an active ingredient, one or two or more substances selected from the group consisting of the aforementioned retinoid and a salt thereof, and a hydrate thereof and a solvate thereof. A preferred effectiveness may sometimes be obtained by administration of two or more different retinoids in combination. As the medicament of the present invention, the aforementioned substance, per se, may be administered. Preferably, the medicament can be administered as a pharmaceutical composition for oral or parenteral administration which can be prepared by a method well known to one of ordinary skill in the art. As pharmaceutical compositions suitable for oral administration, examples include tablets, capsules, powders, subtilized granules, granules, liquids, and syrups. As pharmaceutical compositions suitable for parenteral administration, examples include injections, suppositories, inhalant, eye drops, nasal drops, ointments, creams, and plasters.

The aforementioned pharmaceutical composition can be prepared by adding pharmacologically and pharmaceutically acceptable additives. Examples of the pharmacologically and pharmaceutically acceptable additives include, for example, excipients, disintegrators or disintegrating aids, binders, lubricants, coating agents, dyes, diluents, bases, dissolving agents or dissolving aids, isotonic agents, pH adjusting agents, stabilizing agents, propellants, tackifiers, and the like.

A dose of the medicament of the present invention is not particularly limited. The dose may be suitably increased or decreased depending on various factors to be generally considered such as body weight or age of a patient, kind of a disease and symptoms, route of administration and the like. In general, the medicament may be used within a range of about 0.01 to 1,000 mg per day for an adult for oral administration, which dose may be appropriately increased or decreased.

EXAMPLES

The present invention will be explained more specifically with reference to the example. However, the scope of the present invention is not limited to the following example.

Example 1

Evaluation of Am80 Using Model Rat of Inflammatory Bowel Disease

Male or female Wistar rats weighing 200±5 g were used to create an animal model of inflammatory bowel disease. After the animals were fasted for 24 hours, DNBS (2,4-Dinotrobenzenesulfonic Acid, 30 mg in 0.5 ml 30% ethanol) was instilled intracolonically through the anus. Each of 4-[(5,6,7,8-tetrahydro-5,5,8,8-tetramethyl-2-naphthalenyl)carbamoyl] benzoic acid (Am80, generic name: Tamibarotene) as the medicament of the present invention so as to be a dose at 0.3 mg/kg, and salazosulfapyridine (SASP), a commercially available drug for ulcerative colitis, as a comparative example (positive control drug) so as to be a dose at 300 mg/kg was administered 24 hours before and 2 hours before the DNBS infusion, and once daily for 5 days after 24 hours from the infusion. Tamibarotene or SASP was each administered orally as a suspension in 0.5% carboxymethylcellulose. For the control group, the solvent was administered orally according to the same schedule as that for SASP. The animals were subjected to anatomic examination 24 hours after the final administration, and a degree of bowel inflammation was observed. For each of the Tamibarotene-administered group, SASP-administered group, the normal group, and the control group, five rats were used.

The results are shown in Table 1. The results are indicated as the scores of bowel inflammation (average), weight of the bowel per unit body weight (100 g body weight) (average±standard error), and the number of animals in each group that gave adhesion. The scoring of bowel inflammation were conducted by visual observation according to the method of judgment described in the reference (Am. J. Physiol., 258: G527-34, 1990).

Score of Bowel Ulceration and Inflammation (Macroscopic)

Score: observation

0: Normal;

1: Localized hyperemia, no ulcers;

2: Ulceration without hyperemia or colonic wall thickening;

3: Inflammation and ulceration at one site;

4: Ulcers and Inflammations at two or more sites;

5: A major damaged site extending in 1 cm or longer along the direction of the colon length; and 6-10: When a major damaged site extends in 2 cm or longer along the direction of the colon length, a score is increased by one for each additional 1 cm over 2 cm.

TABLE 1

| Administration Groups (N = 5) | Bowel Inflammation Score [average] | Colon weight/ 100 g body weight [average] | Presence or Absence of Adhesion (in five rats per group) |
|---|---|---|---|
| Normal Group | 0 | 0.288 ± 0.006 | 0/5 |
| Control Group | 5 | 0.916 ± 0.058 | 4/5 |
| Positive Control Group (SASP 300 mg/kg) | 2 | 0.682 ± 0.023 | 2/5 |
| Tamibarotene 0.3 mg Administered Group | 1.8 | 0.728 ± 0.051 | 0/5 |

From the results shown in Table 1, it was found that the score of bowel inflammation and adhesion were significantly suppressed in the group administered with the medicament of the present invention (Tamibarotene, 0.3 mg/kg) as compared with the control group. It was also found that, as for the weight of the colon per unit body weight, an increase of the weight of the colon was significantly suppressed in the group administered with the medicament of the present invention (Tamibarotene, 0.3 mg/kg) as compared with the control group. Further, it was revealed that the medicament of the present invention exhibited the efficacy at a dose of 1/1,000 as compared to that of the positive control drug (SASP). From these experimental results, it can be concluded that the medicament of the present invention significantly suppresses the weight of colon and the score of bowel inflammation as the indexes of inflammatory bowel diseases, and that the medicament is superior to SASP, which has been conventionally used clinically, in suppression of the score of bowel inflammation and adhesion, and is capable of exhibiting sufficient effectiveness at a significantly small dose.

Example 2

Evaluation of Retinoids which Binds to RAR and RXR Using Rat Model of Inflammatory Bowel Disease Male or female Wistar rats weighing 200±5 g were used to create an animal model of inflammatory bowel disease. After the animals were fasted for 24 hours, DNBS (2,4-Dinotrobenzenesulfonic Acid, 30 mg in 0.5 ml 30% ethanol) was instilled intracolonically through the anus. As the medicaments of the present invention, 4-[2,3-(2,5-dimethyl-2,5-hexano)dibenzo[b,f][1,4]thiazepin-11-yl]benzoic acid (HX630) at 3 mg/kg, 4-(5H-7,8,9,10-tetrahydro-5,7,7,10,10-pentamethylbenzo[e]naphtho[2,3-b][1,4]diazepin-13-yl)benzoic acid (LE135) at 5 mg/kg, or a combination of 0.1 mg/kg of Am80 and 3 mg/kg of HX630 were used, and as a comparative example (positive control drug), 300 mg/kg of salazosulfapyridine (SASP) as a commercially available drug for ulcerative colitis was used, and each drug was administered 24 hours before and 2 hours before the DNBS infusion, and once daily for 5 days after 24 hours from the infusion. Each drug was administered orally as a suspension in 0.5% carboxymethylcellulose. For the control group, the solvent was administered orally according to the same schedule. The animals were subjected to anatomic examination 24 hours after the final administration, and a degree of bowel inflammation was observed. For each of the Tamibarotene-administered group, SASP-administered group, the normal group, and the control group, five rats were used.

The results are shown in Table 1. The results are indicated as the scores of bowel inflammation (average), weight of the colon per unit body weight (100 g body weight) (average±standard error), and the number of animals in each group that gave adhesion. The scoring of bowel inflammation were conducted by visual observation according to the method of judgment described in the reference (Am. J. Physiol., 258: G527-34, 1990).

Score of Bowel Ulceration and Inflammation (Macroscopic)
Score: observation
0: Normal;
1: Localized hyperemia, no ulcers;
2: Ulceration without hyperemia or colonic wall thickening;
3: Inflammation and ulceration at one site;
4: Ulcers and Inflammations at two or more sites;
5: A major damaged site extending in 1 cm or longer along the direction of the colon length; and
6-10: When a major damaged site extends in 2 cm or longer along the direction of the colon length, a score is increased by one for each additional 1 cm over 2 cm.

TABLE 2

| Administration Groups (N = 5) | Bowel Inflammation Score [average] | Colon weight/ 100 g body weight [average] | Presence or Absence of Adhesion (in five rats per group) |
|---|---|---|---|
| Normal Group | 0 | 0.248 ± 0.008 | 0/5 |
| Control Group | 4.2 | 0.892 ± 0.046 | 3/5 |
| HX630 (3 mg/kg) Administered Group | 3.4 | 0.763 ± 0.057 | 1/5 |
| LE135 (5 mg/kg) Administered Group | 2.4 | 0.735 ± 0.039 | 0/5 |
| Am80 (0.1 mg/kg) and HX630 (3 mg/kg) Administered Group (combination) | 2.6 | 0.714 ± 0.048 | 2/5 |

From the results shown in Table 2, it can be understood that the colon weights per unit body weight were significantly reduced in the groups administered with HX630 as a retinoid bound to RXR and with LE135 as a retinoid bound to RARα, each alone or in combination, as compared to the control group. From these results, these compounds are concluded to be effective as medicaments for preventive and/or therapeutic treatment of bowel disease.

INDUSTRIAL APPLICABILITY

The medicament of the present invention is capable of exhibiting excellent preventive and/or therapeutic effect against bowel diseases such as inflammatory bowel diseases. In particular, the medicament is characterized to have extremely superior preventive and/or therapeutic effect against inflammatory bowel disease including Crohn's disease for which no effective drug therapy has so far been provided.

What is claimed is:

1. A method for suppressing adhesion of the intestines or therapeutic treatment of adhesion of the intestines comprising administering to a patient in need thereof a therapeutically effective amount of 4-[(5,6,7,8-tetrahydro-5,5,8,8-tetramethyl-2-naphthalenyl)carbamoyl]benzoic acid.

2. The method according to claim 1 wherein the intestines comprise the large intestine.

3. The method according to claim 2 wherein the adhesion of the large intestine is caused by inflammation.

4. The method according to claim 3 wherein the suppressing adhesion of the intestines or therapeutic treatment of adhesion of the intestines is therapeutic treatment of adhesion of the intestines.

5. The method according to claim 2 wherein the suppressing adhesion of the intestines or therapeutic treatment of adhesion of the intestines is therapeutic treatment of adhesion of the intestines.

6. The method according to claim 5, wherein the adhesion is caused by an inflammatory bowel disease.

7. The method according to claim 2, wherein the adhesion is caused by an inflammatory bowel disease.

8. The method according to claim 1 wherein the intestines comprise the small intestine.

9. The method according to claim 8 wherein the adhesion of the small intestine is caused by inflammation.

10. The method according to claim 8 wherein the suppressing adhesion of the intestines or therapeutic treatment of adhesion of the intestines is therapeutic treatment of adhesion of the intestines.

11. The method according to claim 10, wherein the adhesion is caused by an inflammatory bowel disease.

12. The method according to claim 8, wherein the adhesion is caused by an inflammatory bowel disease.

13. The method according to claim 1 wherein the adhesion of the intestines is caused by inflammation.

14. The method according to claim 13 wherein the suppressing adhesion of the intestines or therapeutic treatment of adhesion of the intestines is therapeutic treatment of adhesion of the intestines.

15. The method according to claim 13 wherein the suppressing adhesion of the intestines or therapeutic treatment of adhesion of the intestines is suppressing adhesion of the intestines.

16. The method according to claim 1 wherein the suppressing adhesion of the intestines or therapeutic treatment of adhesion of the intestines is suppressing adhesion of the intestines.

17. The method according to claim 16, wherein the adhesion is caused by an inflammatory bowel disease.

18. The method according to claim 1 wherein the suppressing adhesion of the intestines or therapeutic treatment of adhesion of the intestines is therapeutic treatment of adhesion of the intestines.

19. The method according to claim 18, wherein the adhesion is caused by an inflammatory bowel disease.

20. The method according to claim 1, wherein the adhesion is caused by an inflammatory bowel disease.

* * * * *